United States Patent [19]

Mikulski et al.

[11] Patent Number: 5,540,925
[45] Date of Patent: Jul. 30, 1996

[54] COMPOSITIONS COMPRISING ONCONASE (TM) AND STELAZINE (TM) OR TAMOXIFEN (TM)

[75] Inventors: Stanislaw M. Mikulski, Essex Fells; Wojciech J. Ardelt, Passaic, both of N.J.

[73] Assignee: Alfacell Corporation, Bloomfield, N.J.

[21] Appl. No.: 283,969

[22] Filed: Aug. 1, 1994

Related U.S. Application Data

[63] Continuation of Ser. No. 938,307, Aug. 28, 1992, abandoned, which is a continuation of Ser. No. 526,314, May 18, 1990, abandoned, which is a continuation-in-part of Ser. No. 436,141, Nov. 13, 1989, abandoned, which is a continuation-in-part of Ser. No. 178,118, Apr. 6, 1988, Pat. No. 4,882,421.

[51] Int. Cl.$^6$ ............................ A61K 38/43; C12N 9/22
[52] U.S. Cl. .......................... 424/94.6; 435/199; 530/350; 514/12
[58] Field of Search ........................... 424/94.6; 435/199; 530/350; 514/12

[56] References Cited

U.S. PATENT DOCUMENTS

| | | | |
|---|---|---|---|
| 4,195,017 | 3/1980 | Bogoch | 530/300 |
| 4,882,421 | 11/1989 | Shogen et al. | 530/350 |
| 4,888,172 | 12/1989 | Szebenyi et al. | 424/105 |

OTHER PUBLICATIONS

Embase Abstract No.: 93284537. Phase I human clinical trial of ONCONASE (R) (P–30 protein) administered intravenously on a weekly schedule in cancer patients with solid tumors, Mikulski S. M.; Grossman A. M.; Carter P. W.; Shogen K.; Costanzi J. J., Int. J. ONCOL. (Greece), 1993, Mar. 1 (57–64).

McClay et al. 1988. Semin Oncol. 15(6):569–577 (Abstract Only), Dialog File 155 accession No. 8908 4596.

Hird et al. 1990. Genes and Cancer, John Wiley & Sons, Ltd., Corney et al. (eds). pp. 183–189, N.Y.

Mikulski et al. May 1990. Cell Tissue Kinet. 23:237–246.

Ardelt et al. 1991. J. Biol. Chem. 266(1):245–251.

*Primary Examiner*—Robert A. Wax
*Assistant Examiner*—K. Cochrane Carlson

[57] ABSTRACT

A pharmaceutical to be sold under the ONCONASE trademark, as described in pending commonly owned application application Ser. No. 07/436,141 filed Nov. 13, 1989 is combined with other drugs sold under the trademarks TAMOXIFEN and STELAZINE. The combination of ONCONASE with TAMOXIFEN has unexpected bioactivity in vitro against ASPC-1 human pancreatic adenocarcinoma cells and the combination of ONCONASE with STELAZINE has unexpected bioactivity in vitro against A-549 human lung carcinoma cells.

2 Claims, 1 Drawing Sheet

FIG. 1

| ONCONCASE DOSE (µg/ml) | 0.05 | 0.5 | 5.0 | 10.0 | 20.0 | ED$_{50}$ |
|---|---|---|---|---|---|---|
| ONCONCASE ALONE | 0 | 0 | 9.0 | 34.6 | 53.4 | 18.720 |
| ONCONCASE + 2.5 µM STELAZINE | 0 | 0 | 14.7 | 39.4 | 60.4 | 14.490 |
| ONCONCASE + 5 µM STELAZINE | 1.1 | 2.3 | 24.0 | 50.2 | 70.2 | 12.330 |
| ONCONCASE + 10 µM STELAZINE | 90.8 | 90.8 | 92.3 | 93.6 | 93.8 | 0.027 |
| | | | | | (STELAZINE ALONE) | |
| ED$_{50}$ - STELAZINE | 5.500 | 5.500 | 4.980 | 2.530 | 1.130 | 5.790 |

FIG. 2

| ONCONCASE DOSE (µg/ml) | 0.05 | 0.5 | 5.0 | 10.0 | 20.0 | ED$_{50}$ |
|---|---|---|---|---|---|---|
| ONCONCASE ALONE | 8.1 | 11.8 | 34.8 | 52.0 | 77.9 | 6.818 |
| ONCONCASE + 1 µM TAMOXIFEN | 30.1 | 48.8 | 79.5 | 86.5 | 94.2 | 0.337 |
| ONCONCASE + 3.3 µM TAMOXIFEN | 50.0 | 85.0 | 96.9 | 96.8 | 97.6 | 0.035 |
| ONCONCASE + 10 µM TAMOXIFEN | 96.0 | 97.9 | 96.8 | 98.6 | 99.0 | 0.026 |
| | | | | | (TAMOXIFEN ALONE) | |
| ED$_{50}$ - TAMOXIFEN | 5.734 | 3.625 | 1.876 | 0.891 | 0.682 | 14.751 |

COMPOSITIONS COMPRISING ONCONASE (TM) AND STELAZINE (TM) OR TAMOXIFEN (TM)

This application is a continuation of Ser. No. 07/938,307, filed Aug. 28, 1992, now abandoned, which is a continuation of Ser. No. 07/526,314, filed May 18, 1990, now abandoned, which is a continuation-in-part of Ser. No. 07/436,141, filed Nov. 13, 1989, now abandoned, which is a continuation-in-part of Ser. No. 07/178,118, filed Apr. 6, 1988, now U.S. Pat. No. 4,882,421.

BACKGROUND OF THE INVENTION

The invention relates to pharmaceuticals, and more particularly relates to pharmaceuticals for use in treating cells which cause cancer tumors in humans.

The above-referenced patent application discloses a pharmaceutical which will be referred to herein by the intended trademark ONCONASE. It has now been determined that when this pharmaceutical is used in vitro in a combined therapy with other drugs, the results of the combined therapy are, in certain instances, much more bioactive than would be expected.

One such other drug is marketed under the TAMOXIFEN trademark and another such drug is marketed under the STELAZINE trademark.

BRIEF DESCRIPTION OF THE DRAWINGS

The invention will be better understood with reference to the following illustrative and non-limiting drawings, in which:

Table 1 shows experimental data illustrating how a combined therapy of ONCONASE and STELAZINE has a much greater bioactivity against A-549 human lung carcinoma cells than do either ONCONASE or STELAZINE separately.

Table 2 shows experimental data illustrating how a combined therapy of ONCONASE and TAMOXIFEN has a much greater bioactivity against ASPC-1 human pancreatic adenocarcinoma cells than do either ONCONASE or TAMOXIFEN separately.

DETAILED DESCRIPTION OF PREFERRED EMBODIMENTS

In vitro data indicate that a combination of ONCONASE with a drug sold under the TAMOXIFEN trademark is much more bioactive against human pancreatic ASPC-1 adenocarcinoma than would be expected, given the separate activities of ONCONASE and TAMOXIFEN. In vitro data also indicate that a combination of ONCONASE with a drug sold under the STELAZINE trademark is much more bioactive against human lung A-549 carcinoma than would be expected, given the separate activities of ONCONASE and STELAZINE.

The preferred embodiment of the invention was tested using a cell culture assay. In such an assay, a cell line of known growth rate over a predetermined period is treated with the substance under test and the growth of the treated cells is compared with the growth which would ordinarily be expected from untreated cells.

ONCONASE, described in the above-referenced pending patent application and manufactured in accordance with the methodology described in U.S. Pat. No. 4,882,421 (which methodology is hereby incorporated herein by reference as if fully set forth herein) was dissolved in phosphate buffered saline (PBS) to obtain 1 mg/ml stock solution.

TAMOXIFEN is produced by Sigma Chemical Co., St. Louis Mo. and is a trademark for (Z-1-p-dimethylaminoethoxyphenyl-1, 2-diphenyl-1-butene), citrate salt. In the experiments described herein, TAMOXIFEN was dissolved in absolute ethanol and diluted with RPMI 1640 medium (as produced by Hazleton Research Products, Lenexa, Kans.) to obtain 1 mM stock solution (final concentration of ethanol 11%).

STELAZINE is produced by SK&F Co., subsidiary of SmithKline Beckman Co., Carolina P. R. and is a trademark for (10-[3-(4-methylpiperazin-1-yl)-propyl]-2-trifluoromethylphenothiazine). In the experiments described herein, STELAZINE was diluted with RPMI 1640 medium to obtain 1 mM stock solution.

The assay system utilized the ASPC-1 human pancreatic adenocarcinoma cell line and the A-549 human lung carcinoma cell line; both lines were obtained from the American Type Culture Collection (accession numbers were ATCC CRL 1682 for ASPC-1 and ATCC CCL 185 for A549-). Both cell lines were cultured in RPMI 1640 medium (Hazleton Research Products) and supplemented with 20% (ASPC-1) or 10% (A-549) heat-inactivated fetal bovine serum (Gibco Life Technologies, Grand Island N.Y.) and antibiotic-antimycotic solution composed of: 10,000 units per 1 ml penicillin, 10 mg per 1 ml streptomycin and 25 μg per 1 ml fungizone (complete growth medium). The cells were seeded into 96-well tissue culture plates manufactured by Falcon, of Oxnard, Calif. at a density of 2000 viable cells (50 μl per well) for the A-549 cell line and 4000 viable cells (50 μl) per well for the ASPC-1 cell line. The cell number was based on the previously determined growth curve characteristics for seven days of culture. The cells were allowed to settle for 24 hours and then 50 μl of appropriate ONCONASE and/or TAMOXIFEN or STELAZINE solutions were added per well. The following final concentrations were used:

a) ONCONASE, 20 ng to 10 μg/ml;
b) TAMOXIFEN, 10 μM for ASPC-1 cells; and
c) STELAZINE, 5 μM.

The plates were incubated for an additional six days at 37° C. and 5% carbon dioxide atmosphere. The total assay time was consequently seven days (one day in which the cells are allowed to settle, and six days of incubation). Percentages of viable cells were then determined using the MTT colorimetric assay using the Bio-Rad EIA microtiter plate reader.

The number of cells was determined by a direct count in an AO-Spencer "Brightline" hemocytometer manufactured by Reichert Scientific Instruments in Buffalo, N.Y. with a Neubauer ruling. All solutions used for this purpose were manufactured by Hazleton Research Products. Attached cells were washed three times with Hanks' Balanced Salt Solution and treated with 2 ml of a 0.25% Trypsin—0.02% EDTA solution in buffered saline for about thirty seconds. The solution was removed and the cells were left at 37° C. for 10 minutes, then suspended in 10 ml of the complete growth medium. The 0.25 ml of the cell suspension was diluted with 0.75 ml of the complete growth medium and then 1 ml of 0.5% Trypan Blue solution was added and viable cells were counted.

Tables 1 and 2 present the result of the above experiments. These tables are expressed in mean percent of growth inhibition, i.e. they indicate the effectiveness with which the tested therapies prevented the tested cancer cells from growing over the one week duration of the assay. Thus, a higher number indicates a higher bioactivity against the cell line used in the experiment.

These results demonstrate that, in the instances shown, the bioactivities of ONCONASE combined with STELAZINE in the case of A-549 human lung carcinoma and ONCONASE combined with TAMOXIFEN in the case of ASPC-1 human pancreatic adenocarcinoma are much greater than would be expected from the bioactivities of the individual drugs alone. This may be seen from the $ED_{50}$ figures which are along the right edge of the Tables. These figures represent computed isoeffective doses; the figure shown is the amount of material which would be required to halve the growth rate of the cells undergoing the assay. Thus, the lower the $ED_{50}$ figure, the smaller the dose required to achieve the same bioactivity.

Chemical Analysis and Composition of ONCONASE

ONCONASE has been well characterized chemically. While ONCONASE is a protein isolated from rana pipiens, it is believed that ONCONASE may be produced using genetic engineering techniques, as long as the end result has the following chemistry and structure:

ONCONASE is a pure protein (i.e. homogeneous, as established by standard tests which are used to assay the homogeneity of proteins). By electrophoresis, the molecular weight of ONCONASE is approximately 14,500 Daltons. Calculation of the molecular weight based upon the below listed amino acid sequence indicates that the molecular weight should be 11,819 Daltons. However, because metal ions may have bonded to the protein despite all efforts to remove them, and because different isotopes may be involved, the molecular weight of ONCONASE as determined by mass spectroscopy is 12,430 Daltons. In view of this discrepancy, the molecular weight of ONCONASE as determined by mass spectrometry will be considered to be approximately 12,000 Daltons. ONCONASE has an isoelectric point pI between 9.5 and 10.5, as determined by isoelectric focusing. ONCONASE has a blocked amino terminal group and is essentially free of carbohydrates (as determined by anthrone and orcinol methods).

ONCONASE has the following amino acid composition:

Amino Acid Analysis

| AMINO ACID RESIDUE | MOL % (24 HOUR ACID HYDROLYSIS) |
|---|---|
| Aspartic acid/Asparagine | 13.39 |
| Threonine | 9.84 (Note1) |
| Serine | 8.08 (Note1) |
| Glutamic acid/Glutamine | 5.88 |
| Proline | 3.98 |
| Glycine | 2.98 |
| Alanine | 2.92 |
| Cystine/2 | 7.77 |
| Valine | 7.77 |
| Methionine | 0.94 |
| Isoleucine | 5.29 (Note2) |
| Leucine | 4.95 |
| Tyrosine | 2.85 |
| Phenylalanine | 5.73 |
| Hisitidine | 2.99 |
| Lysine | 11.78 |
| Arginine | 2.85 |
| Tryptophan | Not Determined (Note 3) |
| Approximate Total | 99.99% |

ONCONASE has the following amino acid composition:

Amino Acid Analysis

| AMINO ACID RESIDUE | MOL % (24 HOUR ACID HYDROLYSIS) |
|---|---|

Note 1: Threonine and serine are partially destroyed during hydrolysis and this value is corrected for such partial destruction.
Note 2: This value is corrected for incomplete hydrolysis.
Note 3: Tryptophan cannot be detected in acid hydrolysis of proteins because it is destroyed and is consequently shown as Not Determined. However, analysis of the ultraviolet spectrum revealed the presence of one tryptophan residue per molecule.

Amino Acid Composition (as calculated from amino acid sequence)

| AMINO ACID | NUMBER OF RESIDUES PER MOLECULE OF MATERIAL |
|---|---|
| Aspartic acid | 6 |
| Asparagine | 8 |
| Threonine | 10 |
| Serine | 8 |
| Glutamic acid | 3 |
| Pyroglutamic acid | 1 |
| Glutamine | 2 |
| Proline | 4 |
| Glycine | 3 |
| Alanine | 3 |
| Cystine/2 | 8 |
| Valine | 8 |
| Methionine | 1 |
| Isoleucine | 6 |
| Leucine | 5 |
| Tyrosine | 3 |
| Phenylalanine | 6 |
| Histidine | 3 |
| Lysine | 12 |
| Arginine | 3 |
| Tryptophan | 1 |
| Approximate Total | 104 |

ONCONASE has been sequenced. As is shown below, the total length of the sequence is 104 residues. The N-terminus of the protein is pyroglutamic acid (<Glu). This is a cyclized derivative of glutamic acid which is devoid of the free amino group necessary for direct sequencing and which therefore "blocks" the N-terminus of the protein.

When the shorter fragment described in U.S. Pat. No. 4,882,421 was cleaved with pyroglutamate aminopeptidase, pyroglutamic acid was removed from the shorter fragment, permitting sequencing to commence at the second residue. Such cleavage is a strong indication that the N-terminus is pyroglutamic acid since pyroglutamate aminopeptidase only cleaves pyroglutamic acid. The presence of pyroglutamic acid was further confirmed by mass spectrometry of the referenced shorter fragment. The molecular weight of this shorter fragment determined by mass spectrometry agreed well with the weight as calculated assuming that pyroglutamic acid was present and disagreed with the weight as calculated assuming that glutamic acid was present.

ONCONASE has the following amino acid sequence:

```
 1    2    3    4    5    6    7    8    9    10
<Glu—Asp—Trp—Leu—Thr—Phe—Gln—Lys—Lys—His—

11                                            20
Ile—Thr—Asn—Thr—Arg—Asp—Val—Asp—Cys—Asp—

21                                            30
Asn—Ile—Met—Ser—Thr—Asn—Leu—Phe—His—Cys—
```

```
31                              40
Lys—Asp—Lys—Asn—Thr—Phe—Ile—Tyr—Ser—Arg—

41                              50
Pro—Glu—Pro—Val—Lys—Ala—Ile—Cys—Lys—Gly—

51                              60
Ile—Ile—Ala—Ser—Lys—Asn—Val—Leu—Thr—Thr—

61                              70
Ser—Glu—Phe—Tyr—Leu—Ser—Asp—Cys—Asn—Val—

71                              80
Thr—Ser—Arg—Pro—Cys—Lys—Tyr—Lys—Leu—Lys—

81                              90
Lys—Ser—Thr—Asn—Lys—Phe—Cys—Val—Thr—Cys—

91                              100
Glu—Asn—Gln—Ala—Pro—Val—His—Phe—Val—Gly—

101     104
Val—Gly—Ser—Cys
```

Although a preferred embodiment has been described above, the scope of the invention is limited only by the following claims:

We claim:

1. A bioactive pharmaceutical comprising a protein having the following amino acid sequence:

```
1    2    3    4    5    6    7    8    9    10
<Glu—Asp—Trp—Leu—Thr—Phe—Gln—Lys—Lys—His—

11                              20
Ile—Thr—Asn—Thr—Arg—Asp—Val—Asp—Cys—Asp—

21                              30
Asn—Ile—Met—Ser—Thr—Asn—Leu—Phe—His—Cys—

31                              40
Lys—Asp—Lys—Asn—Thr—Phe—Ile—Tyr—Ser—Arg—

41                              50
Pro—Glu—Pro—Val—Lys—Ala—Ile—Cys—Lys—Gly—

51                              60
Ile—Ile—Ala—Ser—Lys—Asn—Val—Leu—Thr—Thr—

61                              70
Ser—Glu—Phe—Tyr—Leu—Ser—Asp—Cys—Asn—Val—

71                              80
Thr—Ser—Arg—Pro—Cys—Lys—Tyr—Lys—Leu—Lys—

81                              90
Lys—Ser—Thr—Asn—Lys—Phe—Cys—Val—Thr—Cys—

91                              100
Glu—Asn—Gln—Ala—Pro—Val—His—Phe—Val—Gly—

101     104
Val—Gly—Ser—Cys
``` and the citrate salt of (Z-1-p-dimethylaminoethoxyphenyl-1, 2-diphenyl-1-butene).

2. A bioactive pharmaceutical comprising a protein having the following amino acid sequence:

```
1    2    3    4    5    6    7    8    9    10
<Glu—Asp—Trp—Leu—Thr—Phe—Gln—Lys—Lys—His—

11                              20
Ile—Thr—Asn—Thr—Arg—Asp—Val—Asp—Cys—Asp—

21                              30
Asn—Ile—Met—Ser—Thr—Asn—Leu—Phe—His—Cys—

31                              40
Lys—Asp—Lys—Asn—Thr—Phe—Ile—Tyr—Ser—Arg—

41                              50
Pro—Glu—Pro—Val—Lys—Ala—Ile—Cys—Lys—Gly—

51                              60
Ile—Ile—Ala—Ser—Lys—Asn—Val—Leu—Thr—Thr—

61                              70
Ser—Glu—Phe—Tyr—Leu—Ser—Asp—Cys—Asn—Val—

71                              80
Thr—Ser—Arg—Pro—Cys—Lys—Tyr—Lys—Leu—Lys—

81                              90
Lys—Ser—Thr—Asn—Lys—Phe—Cys—Val—Thr—Cys—

91                              100
Glu—Asn—Gln—Ala—Pro—Val—His—Phe—Val—Gly—

101     104
Val—Gly—Ser—Cys
``` and (10-[3-(4-methylpiperazin-1-yl)-propyl]-2-trifluoromethylphenothiazine).

* * * * *